US008589083B2

(12) United States Patent
Prabhakarpandian et al.

(10) Patent No.: US 8,589,083 B2
(45) Date of Patent: Nov. 19, 2013

(54) SYNTHETIC MICROFLUIDIC MICROVASCULATURE NETWORKS

(75) Inventors: Balabhaskar Prabhakarpandian, Madison, AL (US); Shivshankar Sundaram, Tampa, FL (US); Kapil Pant, Huntsville, AL (US)

(73) Assignee: CFD Research Corporation

( * ) Notice: Subject to any disclaimer, the term of this patent is extended or adjusted under 35 U.S.C. 154(b) by 0 days.

(21) Appl. No.: 13/332,400

(22) Filed: Dec. 21, 2011

(65) Prior Publication Data

US 2012/0330629 A1 Dec. 27, 2012

Related U.S. Application Data

(62) Division of application No. 12/428,134, filed on Apr. 22, 2009, now Pat. No. 8,175,814, which is a division of application No. 11/393,715, filed on Mar. 31, 2006, now Pat. No. 7,725,267.

(51) Int. Cl.
*G01N 33/48* (2006.01)

(52) U.S. Cl.
USPC .......... 702/19

(58) Field of Classification Search
USPC .......... 702/19
See application file for complete search history.

(56) References Cited

PUBLICATIONS

Fenton et al. ,"Microcirculatory Model Relating to Geometrical Variation to Changes in Pressure and Flow Rate", Annals of Biomedical Engineering (1981) vol. 9, pp. 303-321.*

Tan et al., "Microfluidic Patterning of Cellular Biopolymer Matricies for Biomimetic 3-D Structures", Biomedical Microdevices (2003) vol. 5, No. 3, pp. 235-244.*

Dickerson et al., "Limited Adhesion of Biodegradable Microspheres to E- and P-Selectin Under Flow",Biotechnology and Bioengineering (2001) vol. 73, issue 6, pp. 500-509.*

* cited by examiner

*Primary Examiner* — Jerry Lin
(74) *Attorney, Agent, or Firm* — Maschoff Brennan, PLLC

(57) ABSTRACT

A synthetic microfluidic microvasculature network and associated methods mimic the structure, fluid flow characteristics, and physiological behavior of physiological microvasculature networks. Computational methods for simulating flow and particle adherence in synthetic and physiological microvascular systems and methods for determining parameters influencing particle adhesion and drug delivery are described with applications in the optimization of drug delivery and microvascular treatments and in describing disease mechanisms that affect the microvasculature.

20 Claims, 14 Drawing Sheets

*Figure 7. Perfusion Studies in Realistic Microvascular Networks Experiments (top) Simulations (bottom)*

SYNTHETIC MICROFLUIDIC MICROVASCULATURE NETWORKS

CROSS-REFERENCE TO RELATED APPLICATIONS

This application is a divisional of and claims priority under 35 U.S.C. 121 to U.S. application Ser. No. 12/428,134 filed Apr. 22, 2009 now U.S. Pat. No. 8,175,814, which is a divisional of U.S. application Ser. No. 11/393,715 filed Mar. 31, 2006, now U.S. Pat. No. 7,725,267 which is incorporated by reference in its entirety for all purposes.

STATEMENT REGARDING FEDERALLY SPONSORED RESEARCH

The U.S. Government may have certain rights in this invention pursuant to SBIR Contract Number 1R43HL076034-01A1 awarded by the National Institutes of Health.

BACKGROUND OF THE INVENTION

1. Field of the Invention

The present invention relates to microfluidic systems that mimic the structure, fluid flow characteristics, and physiological behavior of small physiological vessels such as those found in the microvasculature. The invention has many uses including the optimization of drug delivery and microvascular treatments and in describing disease mechanisms that affect the microvasculature such as inflammation, diabetes and hypertension. The invention is not limited to vessels of the circulatory system but is applicable to all physiological vessels such as lymphatic vessels and glandular ductules.

2. Description of Related Art

Physiological microvascular networks are series of interconnected arterioles, capillaries, and/or venules. The diameters of these vessels range from about 2-10 μm for capillaries and about 10-100 μm for arterioles and venules. In the context of the present invention, the term "microvascular networks" can also be used to describe networks of physiological vessels having diameters of less than about 100 μm such as renal or seminiferous tubules.

A considerable body of work has been developed regarding in-vitro systems for the study of vascular endothelial responses, leukocyte adhesion, and drug carrier delivery in the presence of flow. For example, in-vitro flow chambers have facilitated the identification of biological molecules involved in the adhesion of leukocytes to the endothelium. It is now known that the dynamics of cell adhesion to vascular endothelial cells are controlled by a combination of biochemical and macro-properties such as vessel size and flow rate. These results have led in part to an effort to understand endothelial cell-leukocyte interactions using carefully controlled in-vitro flow cell experiments.

The adhesion of particles such as leukocytes, platelets, liposomes/lipisomes, and microencapsulated drug carriers to microvascular endothelium is also greatly influenced by the geometric features of the vasculature, local hemodynamics, and numerous receptor-ligand interactions between endothelial cells and particles. Local hemodynamic factors associated with microvascular geometry such as wall shear stress, pressure, and residence time influence the rates, amounts, and distributions of particle adhesion as well as endothelial cell morphology and function. This complex interplay between flow, cells, and particles is still poorly understood and it is not possible to predict, for example, adhesion patterns and numbers of adhered particles in the microvasculature based on current in-vitro flow cell technologies. The present invention advances in-vitro flow cell technology so that adhesion patterns and numbers of adhered particles in the microvasculature, for example, can be predicted.

In-vitro flow chambers typically comprise a single flow channel formed by two plates or slides separated by a gap. The cross section of the flow channel is typically a flat rectangle with constant dimensions. The flow chambers are usually transparent and are perfused at low Reynolds numbers to match wall shear stresses observed in blood vessels in-vivo. The lower plates of these flow chambers are coated with either protein or adherent endothelial cells to simulate the surface properties of physiological vessels. The chambers are typically mounted on a microscope stage and events are recorded with a high-speed camera and stored for subsequent analysis.

Efforts to construct microfluidic flow chambers typically feature linear channels with conventional rectangular cross sections and constant cross sectional areas. For example, Lu et al. (2004) reports the fabrication of a device on PDMS for varying shear profiles. Unlike the present invention, this and other existing device do not account for the geometric variations and the interconnectedness found in microvascular networks and lack the ability to effectively reproduce or simulate the flow patterns and particle adhesion patterns observed in physiological vessels and microvasculature.

The smallest cross section of commercially available in-vitro flow chambers is typically about 2500 μm×125 μm, which is significantly larger than arterioles, capillaries, and venules. They do not provide realistic sizes and geometries corresponding to complex combinations of thoroughfare channels, bifurcations, junctions, convolutions, and/or variable diameters found in in-vivo microcirculation. These complex features determine local fluid dynamic profiles and thereby local values of shear stress, pressure, residence time, and velocity. Complex geometrical features also strongly influence the transport and adhesion of cells and other particles to sites in the microvasculature. In diseased networks such as those affected by tumor growth, stenoses, arteriosclerosis, diabetes, and radiation therapy, both flow profiles and microvasculature features are different from healthy networks. Examples include medullary arteriolar tortuosity seen in hypertension and intraparenchymal arteriolar-to-arteriolar anastomoses in pathological conditions in the cerebrum. Existing in-vitro flow chambers, however, having idealized rectangular or circular duct geometries cannot be modified to reflect changes that occur with disease.

Attempts have been made to improve on the scale of in-vitro microvascular channels. Cokelet et al. (1993) fabricated an in-vitro microvascular channel to study blood flow by photolithography on microscope slide glass. Frame et al. (1995) generated idealized (straight) semi-circular microvascular channels (20-50 μm) on glass to mimic the arteriolar microcirculation. They were also successful in growing endothelial cells on these channels. However, both studied idealized microchannels that did not account for either the interconnectedness or variations found in in-vivo microvascular networks.

The complexity of the flow in microvascular networks necessitates the use of sophisticated models to analyze and understand flow behavior. Mathematical modeling has been used extensively to study particle/cell adhesion in a flow environment. Cozens-Roberts et al. (1990) derived an analytical expression for the shear stress and adhesive force relationships in flow chambers. Hammer and coworkers (1992) developed mathematical models for cell attachment and rolling. The dependence of rolling adhesion of cells on vessel diameters and other parameters has been addressed in several notable works including, Goldsmith & Turitto (1986), Schmid-Schoenbein et al. (1975), House & Lipowsky (1988) and Chapman & Cokelet (1998). The biochemical processes of receptor-ligand attachment have been extensively studied as well (Goetz 1994; Hammer 1992). Chapman & Cokelet (1998) used computational fluid dynamics modeling (CFD) to analyze the hemodynamic impact of leukocytes adherent to the wall of post-capillary venules. Chang et al. (2000) disclosed an "Adhesive Dynamics" technique for studying and developing a state diagram for cell adhesion in flow, under simple conditions.

All of the numerical studies mentioned above are based upon simple, idealized flow chambers with regular geometries and have not examined flow profiles and shear stresses in realistic in-vivo microvasculature scenarios with relevance to cell adhesion. In contrast, the present invention includes a CFD-based model framework that analyzes fluid flow and particle motion/adhesion in the context of realistic in-vivo networks that correspond to the fabricated vascular networks of the invention. The CFD models can be used to analyze and interpret results from experiments and to convert them into information used to assist with the design of experiments and treatment protocols.

In summary, there remains a need in the art for an in-vitro flow chamber that accurately simulates the anatomical and hemodynamic properties of physiological microvascular networks. There is also a need for methods of using such a flow chamber that describe and predict the behavior of particles and cells in microvascular networks. Such a flow chamber and methods can be used, for example, to screen materials and methods for optimal drug delivery to both healthy and diseased microvasculature.

BRIEF SUMMARY OF THE INVENTION

The present invention provides apparatus and methods that can be used to study fluid flow and particle adhesion in physiological vessels including arterioles, capillaries, venules, and microvascular networks comprising any combination of the three. The same apparatus and methods can be used to optimize drug delivery in the microvasculature.

In one aspect, the present invention is a method of predicting the adhesion parameters of particles in a physiological microvascular network or an in-vitro microvascular flow chamber using a computational fluid dynamic (CFD) model.

In another aspect, the present invention is an anatomically realistic, in-vitro/in-silico toolkit to study microvascular processes such as leukocyte adhesion, platelet adhesion, inflammation, chemotaxis, thrombosis, vascular activation, and the effects of shear rate on vascular endothelial cells.

DEFINITIONS

Figure 1:
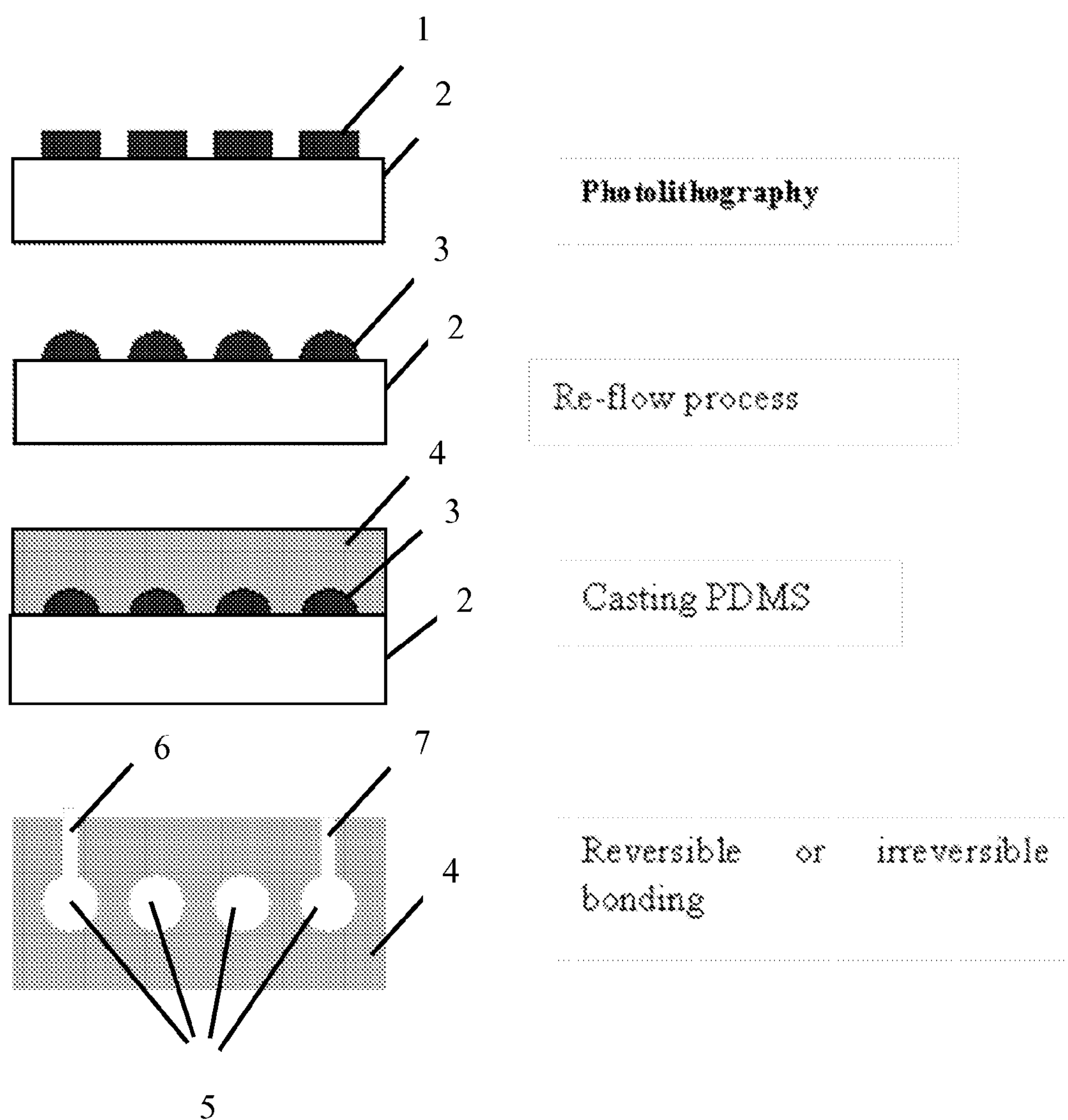
FIG. 1 Casting method for microvascular chip

A "synthetic microvascular network" (SMN) is a man made network that comprises a plurality of interconnected flow channels that form geometrical features and have fluid flow properties found in physiological microvascular networks. The flow channels (synthetic vessels) form intersecting networks and may be arranged end to end, analogous to an arteriole, capillary, venule sequence. Flow channels and the SMNs they form possess one or more geometric characteristics of physiological microvascular selected from variable cross-sectional shapes, variable cross-sectional areas, convolutions, turns, and anastomoses. A network consisting entirely of linear channels with constant cross sectional areas, for example, is not a SMN because such a network does not possess the required physiological characteristics of a physiological microvascular network. One or more flow channels of a SMN may comprise walls made of a porous material such that fluid may move from the interior (lumen) of the flow channel into a space external to the lumen in a manner similar to the movement of fluid from the lumen of a physiological vessel into an interstitial space.

A "microfluidic chip" is constructed using well known techniques employed in the semiconductor industry such as photolithography, wet chemical etching, thin film deposition and soft lithography using polymeric substrates, such as Polydimethylsiloxane (PDMS). In general, a microfluidic chip is formed with a number of microchannels that are connected to a variety of reservoirs containing fluid materials. The fluid materials are driven or displaced within these microchannels throughout the chip using electrokinetic forces, pumps and/or other driving mechanisms.

"Tortuosity" is a measure of the indirectness of a vessel or flow channel path. Tortuosity can be measured in several ways. One exemplary means of measuring tortuosity is to sum the angles between consecutive trios of points along the space curve represented by a vessel skeleton and then normalize by path length. Tortuosity may also be measured, for example, by counting inflection points along each vessel or flow channel and multiplying this number (plus one) times the total path length and then dividing by the distance between the ends of the each vessel or flow path.

DETAILED DESCRIPTION OF THE INVENTION

Preferred embodiments of the present invention are described and illustrated in the drawings. Specific terminology is employed for the sake of clarity but the invention is not intended to be limited to the specific terminology used and it is to be understood that each specific element includes all technical equivalents that operate in a similar manner to accomplish a similar purpose. Each reference cited herein, including each reference cited in the description of related art, is incorporated by reference in its entirety. The terms used herein are intended to have their conventional meanings as understood by a person of ordinary skill in the art, as supplemented by the definitions provided.

The microfluidic microvasculature chips of the present invention comprise at least one fluid inlet, at least one fluid outlet, and at least one SMN. The inventors have demonstrated that the SMNs of the present invention, in contrast to known in-vitro flow chambers, reproduce the fluid flow and particle adhesion patterns observed in physiological microvascular networks. The inventors have also developed simulation software that is capable of analyzing the fluid flow and particle deposition and/or adhesion patterns of microfluidic microvasculature chips and physiological microvascular networks, thereby extracting predictive relationships between critical parameters such as flow rate, particle size, receptor density, and network geometry.

Obtaining Geometries for Making Replicas of Physiological Microvascular Networks Maps of complete microvascular networks are constructed from a collage of arterioles, capillaries and venules. The entire network is digitized by tracing each vessel on the assembled collage in an AutoCad Map® using a computerized drawing board (e.g., Drawing Board III®, CalComp).

After a network is digitized, an AutoCad Map® cleanup routine is used to ensure all vessels are properly connected at their common nodes. A tolerance value is set which distinguished between common nodes and neighboring end points. Each vessel is graphically represented by a polyline consisting of a series of straight lines connected through vertices. The system compares the distance between successive vertices in a polyline to the set tolerance value. The vortex is removed from the polyline if the distance is below the set tolerance value.

To reduce error resulting from the manual tracing of networks from composite images, an automated tracing system such as one using the software package ENVI® (RSI Research Systems, Inc.) can be used. The images traced by ENVI® can then be directly incorporated into and interfaced with databases in Autocad Map®.

Obtaining Geometries for Making Reconstructed "Averaged" Microvascular Networks

The present invention includes not only replicas of physiological microvasculature but also "averaged" or "nominal" micovascular networks based on combinations of several physiological microvascular networks. The term "averaged" is used to indicate that the microvascular network geometry is derived from the geometries of at least two actual microvascular networks. The images are analyzed as described above and subjected to a detailed morphological analysis to yield statistical data of morphometric parameters such as ratios of parent to daughter vessel diameters, branching angles, distances between branches, rations of branch length to branch channel diameter, bifurcation branch density, and recombining branch density. Averaged microvascular networks can be generated by using averaged morphometric data and/or stochastic sampling of probability density functions for morphometric data according to, for example, Kassab et al. (2000). Averaged microvasculoar networks may be generated using values selected from a variety of statistical distributions for individual morphometric parameters. The values used need not be "average," "mean," or "median" values for measured morphometric parameters. Averaged microvascular networks may also be derived from two or more averaged microvascular networks.

Fabrication of SMNs

A digitized network is converted into a mask using standard MEMS techniques. The fabrication procedure (FIG. 1) involves creating a mask layout, fabricating a casting template (e.g., on silicon or glass), and casting using PolyDiMethylSiloxane (PDMS) or other plastic substrates. The process begins with the fabrication of a casting template using the photoresist re-flow method. The photoresist 1 is chosen based upon depth and is spin coated on a silicon or glass substrate 2 and exposed to UV-radiation through a chrome mask to define the channel network. Appropriate spin speed is used to deposit the desired thickness (20-25 μmin this case) of photoresist on the silicon wafer. Re-flow of the photoresist above the melting point results in the formation of curved (rounded) features 3 on the substrate. PDMS elastomer precursor and the curing agent are mixed in a ratio of 10:1. The mixed elastomer 4 is poured against the silicon or glass wafer to generate the negative replica of the features in the template. The mixture is allowed to sit for an hour and is cured on a leveled, flat hot plate at 60° C. for 3 hours. After curing, the PDMS is peeled off from the casting template, which now has semicircular microchannels. Being an elastomer, the PDMS conforms itself to another PDMS wafer having similar semicircular channels. Alignment features are included on the mask to prevent any misalignment during the bonding of two PDMS substrates to complete the circular cross-section microchannels 5. Input and output ports 6 and 7 are drilled on one of the substrates for fluid transport. Optional plasma modifications on PDMS control the nature of bonding, depending on the requirements. Following the creation of a master/template for the microvascular chip, copies can be made in a fast and cost-effective manner. The channels of the SMN have cross-sectional dimensions of between 0.1 μm and 100 μm. Preferably, the dimensions correspond to those of physiological vessels such as about 2-10 μm (capillaries), about 10-100 μm for arterioles and venules, and less than about 100 μm (renal or seminiferous tubules).

Coatings and Cell Cultures in SMNs

Synthetic microvascular networks may be coated with proteins, glycoproteins, proteoglycans, or other substrate molecules to facilitate the growth of cells on the inner surfaces of the networks. Examples of substrate molecules include collagen, gelatin, laminin, and fibronectin. The channels of synthetic microvascular networks may also be coated with adhesion molecules such as P-selectin, E-selectin, ICAM-1, or other receptors to facilitate adhesion of specific cell types or particles such as lipisomes or drug encapsulating or targeting agents. The methods of coating many plastics with proteins and other molecules are known in the art.

It is also possible to culture cells on the inner surfaces of SMN flow channels. SMNs coated with cultured cells can be used to study the adhesion of particles to human microvascular endothelial cells (HMVECs), human umbilical cord vascular endothelial cells (HUVECs), and bovine aortic endothelial cells (BAECs), for example. Virtually any cell type can be cultured in SMNs, depending on the adhesion process being studied. For example, one may screen for cancer targeting molecules in a realistic environment using SMNs coated with the tumor cells being targeted. Libraries of microencapsulated drugs comprising variable targeting molecules can be screened using SMNs coated with the target tumor cells and/or the corresponding virtual SMNs. Tumor cells may also be co-cultured with endothelial cells, for example.

Models and Simulation of Adhesion Process

Some embodiments of the present invention include a computational model for analysis of particle adhesion in microvascular networks. The mathematical formulas used to conveniently describe the computational modeling embodiments of the present invention are not intended to limit the invention to the mathematical formulas used to describe the model. Other mathematical formulas than those presented herein can be expressed alone or in combination to arrive at the same mathematical results.

The present multi-physics, high-fidelity model can be used to study the process of particle adhesion and hydrodynamics in SMNs. Data obtained from such studies can then be used by the same model for in-silico simulation and screening experiments. In addition to particle transport in a Lagrangian frame of reference, the present in-silico model includes the following phenomena: (a) shear-induced lift forces, (b) particle-wall lubrication effects, (c) nanoparticle and porous particle transport, (d) particle-particle interactions, and (e) abstraction of reduced order adhesion models from available detailed formalisms. These elements will be described in more detail.

The shear-induced lift force or Saffman lift force, arises due to the surface pressure distribution on a particle in the presence of a velocity gradient in the flow field and plays an important role in determining deposition and/or adhesion patterns. Generalized Saffman lift force can be expressed as:

$$F_{saff}=C_{Saff}(d_p)^2(\mu_c\rho_c)^{1/2}|\omega_c|^{1/2}[(u_c-u_p)\omega_c] \tag{1}$$

where $\omega_c=\nabla\times u_c$, $u_c$ and $u_p$ are fluid and particle velocity vectors respectively, $C_{Saff}$ is the Saffman lift coefficient, $d_p$ is the particle diameter, and $\mu_c$ and $\rho_c$ are the viscosity and density of the fluid respectively.

To account for lubrication forces, a correction to particle force due to Stokes flow is applied as $$F_H = 6\pi\mu v_p r_p \lambda \tag{2}$$

$$\lambda = \frac{4}{3}\sin\alpha\sum_{n=1}^{\infty}\frac{n(n+1)}{(2n-1)(2n+3)}\left(\frac{2\sinh(2n+1)\alpha+(2n+1)\sinh 2\alpha}{4\sinh^2\left(\frac{n+1}{2}\right)\alpha-(2n+1)^2\sinh^2\alpha}-1\right) \tag{3}$$

where $\mu$ is the fluid viscosity, $v_p$ is the particle velocity, $r_p$ is radius of the particle and $\alpha=\cos h^{-1}(h/r_p)$ where h is the distance between the center of the sphere and the wall. The lubrication force model is extended to include the effect of fluid inertia $$F_H = 6\pi\mu v_p r_p\frac{1}{\varepsilon}\left[1+\frac{1}{5}\left(1+\frac{Re_p}{4}\right)\varepsilon\ln\left(\frac{1}{\varepsilon}\right)\right] \tag{4}$$

where $Re_p$ is the particle Reynolds number and $\epsilon=h/r_p-1$.

Nanoparticles experience Brownian motion due to the impact of carrier fluid molecules on the particles. Brownian force can be evaluated as a stochastic force added to the particle equation of motion $$F_B = m_p R\sqrt{\frac{216}{\pi}\frac{\mu k_B T}{C_c\rho_p^2 d_p^5\Delta t}} \tag{5}$$

where $C_c$ is the Cunningham correction factor and $m_p$ is particle mass, $\rho_p$ is the particle material density, $k_B$ is the Boltzmann constant, T is the absolute temperature, $\Delta t$ is the time step, and R is a Gaussian random number bounded by −1 and +1. The Cunnigham correction factor is defined in terms of the local Knudsen number, which is a measure of the rarefaction effects. For porous particles, the density difference between the particle and the suspending buffer is small and the particle equation of motion has to be modified to take into account the virtual or added mass force.

Particle direct interactions are critical to particle dynamics in that they introduce a dispersive and dissipative element to the particle equation of motion. The inventors have developed efficient algorithms to compute particle collisions using local neighborhood search methods. The algorithm takes advantage of the fact that particles travel with finite velocity and computational time steps are small. Therefore, colliding particles are almost always in physical proximity. A pre-specified search level determines the number of neighboring particles amongst which collisions are enacted. The most basic search level restricts the number of neighboring particles as the number contained by a cell whereas higher search levels utilize the available cell-face grid connectivity information to prepare a list of neighboring cells. Hard sphere collisions are then enacted amongst all the particles contained in the volume defined by these neighboring cells.

The known models of particle adhesion are largely based on interpreting the ligand-receptor complexation as a reversible process $$A_f \underset{k_b}{\overset{k_f}{\rightleftharpoons}} A_b \tag{6}$$

where $A_f$ and $A_b$ are the free and bound receptor molecule states, respectively and $k_f$ and $k_r$ are the bond formation and bond rupture constants, respectively. Let $n_f$ and $n_b$ the surface densities of the free and bound receptor molecules, so that the total number density of receptor molecules is given by $n_r=n_b+n_f$ for independent, homogeneous ligand-receptor interactions. Bond formation and particle adhesion is modeled using either (a) deterministic or (b) stochastic kinetics. In deterministic methods, time evolution of bond density can be solved using $$\frac{dn_b}{dt} = k_f(n_r-n_b)(n_l-n_b)-k_r n_b \tag{7}$$

where $n_l$ is the ligand number density. The bond rupture rate constant is described as an exponential function of the force acting on the bonds $$k_r = k_r^0\exp\left[\frac{\gamma f}{k_B T}\right] \tag{8}$$

where $k_r^0$ is the zero-force (unstressed) rate constant, $\gamma$ is the bond interaction parameter, $k_B$ is the Boltzmann constant and T is the absolute temperature. Typically, the forward rate constant is taken to be independent of force. An adhesion criteria based on number of closed bonds, the bond strength and fluidic forces on the particle is used to determine capture. A stochastic formalism takes advantage of the fact that particle adhesion in fluidic systems is a discrete process. Therefore the stochastic dynamics of an aggregate formation can be described by a one-step Master Equation $$\frac{dp_n}{dt} = G(n-1)p_{n-1}+R(n+1)p_{n+1}-[G(n)+R(n)]p_n \tag{9}$$

where $p_n$ is the probability that n bonds are closed at time t. The forward and reverse transition rates between the possible states are postulated based on assumptions similar to the Bell model and the probability of adhesion is computed from $P_f=1-p_0$ where $p_0$ is the probability that zero bonds are closed (unbonded state).

Examples: Digitization of Cremaster Muscle Microvasculature

Figure 2:
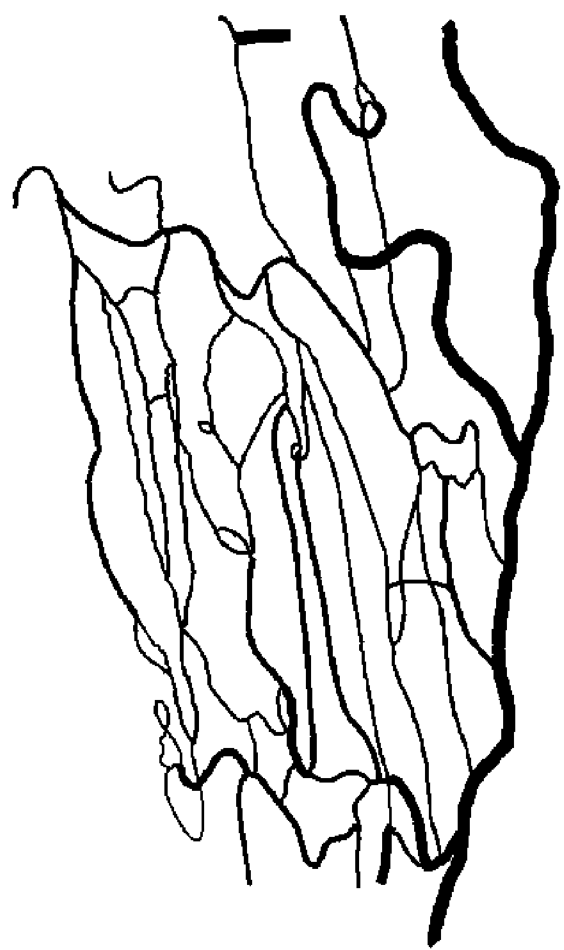
FIG. 2 Digitized microvascular network

One example of a physiological (in-vivo) micovascular network can be found in the cremaster muscle. The cremaster muscle model has been used to study microvascular networks and particle/cell interaction with vessel walls under normal and pathological conditions. These networks tend to be 2D in nature. The network shown in FIG. 2 was digitized according to methods explained herein. The digitized networks include data on various parameters including inlet/outlet branches, flow rates, shear stress, diameter, distance between nodes, and vessel length, as well as the topology of the network.

Figure 3:
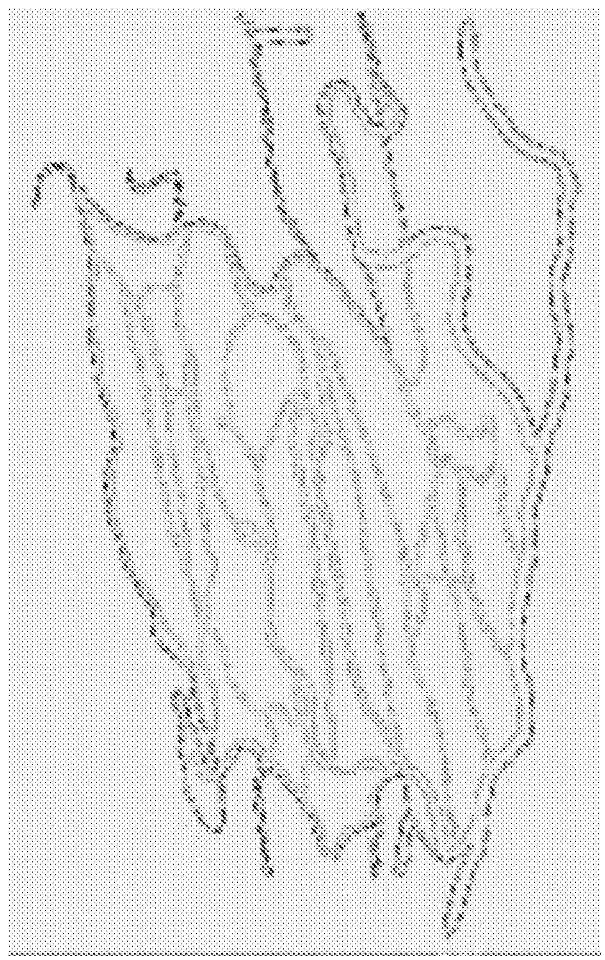
FIG. 3 Vectorized digital microvascular network

Two microvascular networks comprising normal and diseased (irradiated) tissues were used to generate microvascular networks from the database of networks in the cremaster muscles of hamsters. The networks were rendered via an automated digitization algorithm implemented using the software package Arc-Info® (ESRI). The arc-node topology feature in Arc-Info® was used to digitize the cremaster microvascular network shown in FIG. 2 to automatically map the vessels. The image was then vectorized to obtain the image in FIG. 3 with the associated files, which contain the connectivity information of the network. The accuracy of this system in digitizing the networks can be seen from a comparison of the two images. The information on the vectorized image is in GIS format and was directly incorporated into an ANET® system and used for modeling purposes.

Examples: Application of the Computational Model

Simulation of particle adhesion and dye perfusion in microfluidic environs requires that fluid flow, scalar transport and particle dynamics be solved in a coupled fashion. Fluid flow in microfluidic channels is described by the conservation of mass and momentum (Naviér-Stokes) equations:

$$\frac{\partial u_i}{\partial x_i} = 0 \tag{10}$$

$$\frac{\partial \rho_c u_i}{\partial t} + \frac{\partial \rho_c u_j u_i}{\partial x_j} = -\frac{\partial P}{\partial x_i} + \frac{\partial \tau_{ij}}{\partial x_j} + \rho_c g_i \tag{11}$$

where u, $\rho_c$, P and g are the fluid velocity, density, pressure and gravity respectively. Fluid shear stress ($\tau_{ij}$) is expressed in terms of the basic variables using constitutive relations. Dye perfusion is modeled by solving a convective-diffusive transport equation for a passive scalar:

$$\frac{\partial C_j}{\partial t} + \frac{\partial u_i C_j}{\partial x_i} = D_j \frac{\partial^2 C_j}{\partial x_i x_i} \tag{12}$$

where $C_j$, and $D_j$ are the dye concentration and diffusivity respectively. Particle motion is tracked in a Lagrangian (following the particle) fashion:

$$\frac{\partial v_i}{\partial t} = \frac{f}{\tau_v}(u_i - v_i) + g_i \tag{13}$$

where f and $\tau_v$ are the particle friction factor and aerodynamic response time respectively and g is the body force.

Modeling of particle/cell adhesion has been investigated by several researchers with the developed models largely applicable to the adhesion of a single (or few) particle to the surface. The analysis software of the present invention calls for computationally efficient investigations of the adhesion of thousands of particles in complex flow situations. Therefore, a simplified adhesion model based on the inherently stochastic nature of particle/cell adhesion is employed. In this model, particle/cell adhesion is described as a probabilistic process, where the probability of particle adhesion is given by $$P=\exp(-G/G_c) \tag{14}$$

where G is the local shear rate and $G_c$ is the critical shear rate. The critical shear rate is a function of particle size, as well as minimum and maximum bond length to represent the biochemical system. The functional form for the critical shear rate is taken to be:

$$G_c = K(\sin\Theta)^3 \tag{15}$$

where $$\Theta = \cos^{-1}\left[1 - \frac{2(H-h)}{d_p}\right] \tag{16}$$

where K is a constant for a given receptor-ligand pair, H and h are the maximum and minimum bond length respectively and $d_p$ is the particle diameter. This functional form of the critical shear rate has been experimentally verified.

Figure 4:
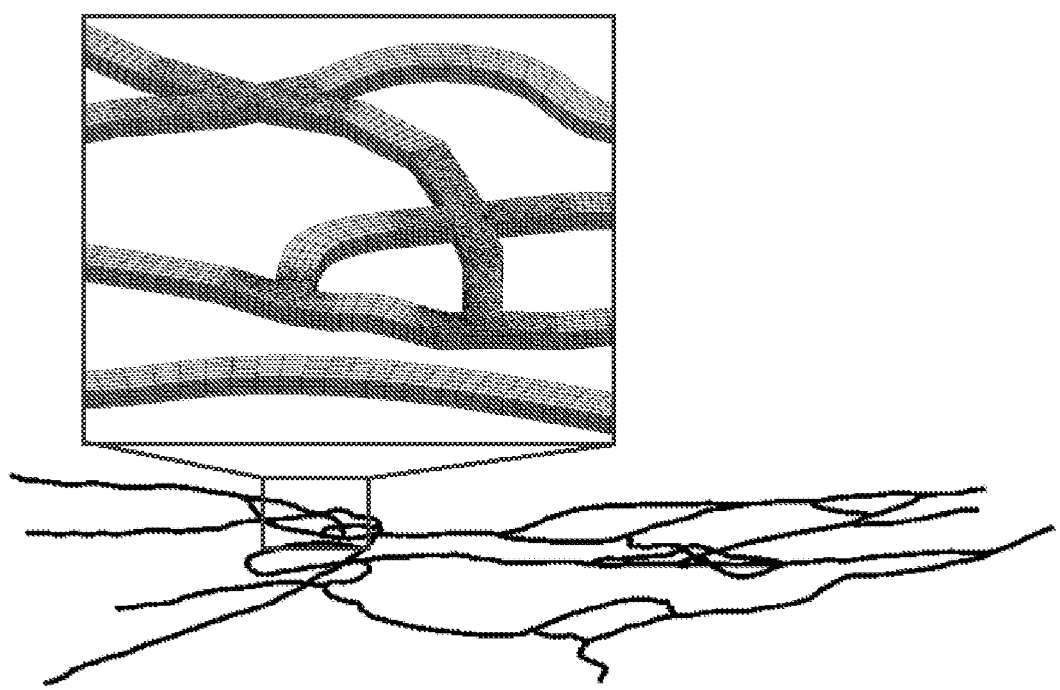
FIG. 4 Computational mesh for microvascular networks

A general-purpose Computational Fluid Dynamics (CFD) code, CFD-ACE+® (ESI Group), based on the Finite Volume Method (FVM) is used to discretize and solve the governing equations. CFD-ACE+® uses a pressure-based methodology for integration of Naviér-Stokes equations on arbitrary mesh topologies using a finite volume approach. An iterative solution procedure based on a SIMPLE-C algorithm is used to obtain a converged solution for fluid flow, dye transport and particle motion. CFD-ACE+® has been extensively validated and demonstrated for microfluidic systems as well as adhesion calculations. Particle adhesion studies in simple bifurcation were facilitated by python scripting-based computational mesh generation and problem definition capabilities available within the simulation framework. Computational meshes for the microvascular networks were created by importing network layouts in DXF format into CFD-GEOM® (ESI Group), the grid generation module of CFD-ACE+®. A three dimensional hybrid mesh comprising of hexahedral and prismatic elements, was created for simulation and analysis. Mesh refinement studies were performed to establish grid independence and the final computational domain consisted of approximately 160,000 cells (FIG. 4).

Examples: Microfabrication of Microvascular Networks

Synthetic microfluidic networks of semicircular cross section channels were prototyped using conventional photo and soft lithography techniques. Layouts of the digitized network images as well as idealized bifurcations were rendered in AutoCAD LT® (AutoDesk). The AutoCAD® designs were printed at high resolution on Mylar film, which was then used as a mask for UV patterning to the desired thickness of positive resist spun on top of a silicon wafer. An adhesion promoter was used to enhance the strength of bonding of the photoresist on the silicon wafer. After developing for 3 min in developer, the photoresist was overflown by heating at 180° C. for 2 minutes on a hotplate, producing the semicircular mold structures.

PolyDiMethylSiloxane (PDMS) was chosen for replicating the microfluidic devices from the master, on account of its gas permeability (beneficial for cell culture), optical transparency, ease of casting, and disposable nature. Other materials that may be used in place of PDMS include SBS—Poly (Styrene Butadiene Styrene), SEBS—Poly(Styrene-Ethylene-Butadiene-Styrene) elastomers, Polyester-ether (PEE) thermoplast and thermoset polyester (TPE), which can be used for replica molding fabrication techniques. Polyolefin plastomer (POP's) can be specifically used for submicron range channels. Glass or quartz with reactive wet/dry etching of the microchannels can also be used.

Thermoplastic materials such as polymethylmethacrylate (PMMA), polycarbonate (PC), cyclic olefin copolymer (COC), polystyrene (PS), poly vinyl chloride (PVC), and polyethylene terephthalate glycol (PETG) can be used with embossing techniques or injection molding. PS, PC, cellulose acetate, polyethylene terephthalate (PET), PMMA, PETG, PVC, PC, and polyimide can also be used with laser ablation techniques. PDMS was prepared according to the manufacturer's instructions and cast over the photoresist mold to create complementary microchannels in PDMS. Inlets and outlets were punched using a beveled 25-gauge needle. The bonding surfaces of the PDMS and a regular 1×3 inches glass slide were treated with oxygen plasma produced in a parallel plate plasma asher. A good seal between the PDMS and glass was achieved by heating the assembly at 75° C. for 10 minutes on a hotplate. Tygon Microbore® tubing with an outside diameter of 0.03 inch and inner diameter of 0.01 inch was used to connect a 30 gauge stainless steel needle, which served as the connecting port to a programmable syringe pump.

Examples: Perfusion and Particle Transport

Trypan blue was injected into the inlet port of the SMN at a flow rate of 0.05 μl/min. An epi-fluorescence inverted microscope with a 4× objective equipped with a motorized stage controlled by a computer was used to automatically obtain images from adjacent microscope fields, which were digitally combined. These images were then used to form a 6×6 montage of the fabricated microvascular network to determine the flow path in the network. This flow path was then compared with simulation flow paths for validation of the predicted routes in the simulation.

2 μm fluorescent particles were injected at a flow rate of 0.05 μl/min at a concentration of $4\times10^6$ particles/ml into the inlet of a physiological microvascular network. Particle transport in the network was visualized using an inverted epi-fluorescent microscope and recorded using a cooled CCD camera. Particle flux at selected major junctions was estimated by counting the number of particles entering the junction as well as the number of effluent particles over a 30 second time interval. Readings were repeated to arrive at a statistical average.

Examples: Perfusion and Particle Transport Simulation

Figure 5:
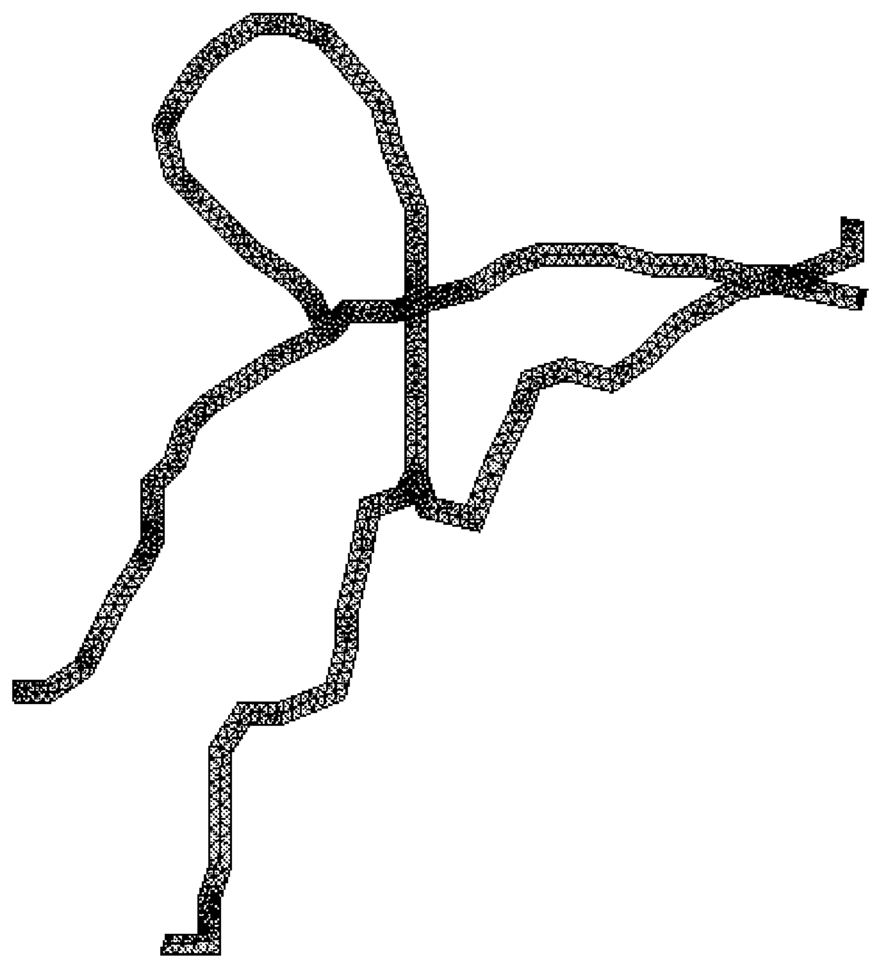
FIG. 5A Computational Domain of a SMN
FIG. 5B Simulated Pressure levels in a SMN
FIG. 5C Simulated Shear Stress levels a SMN
Figure 5:
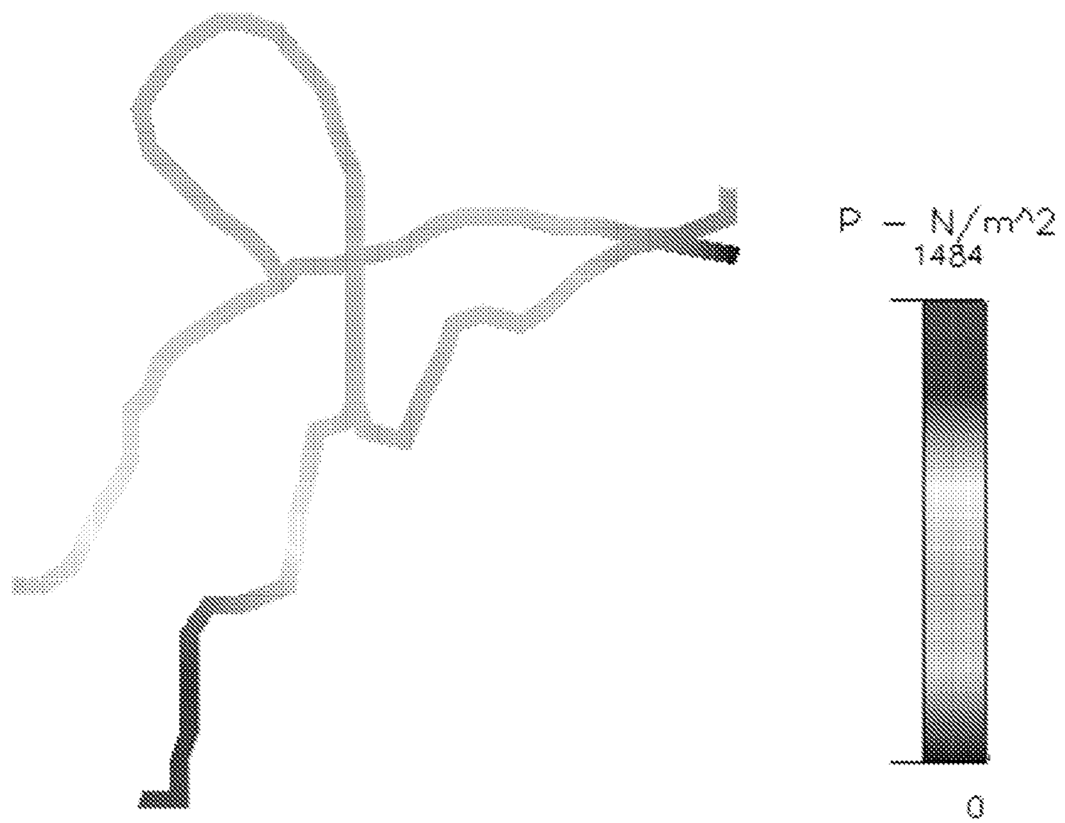
Figure 5:
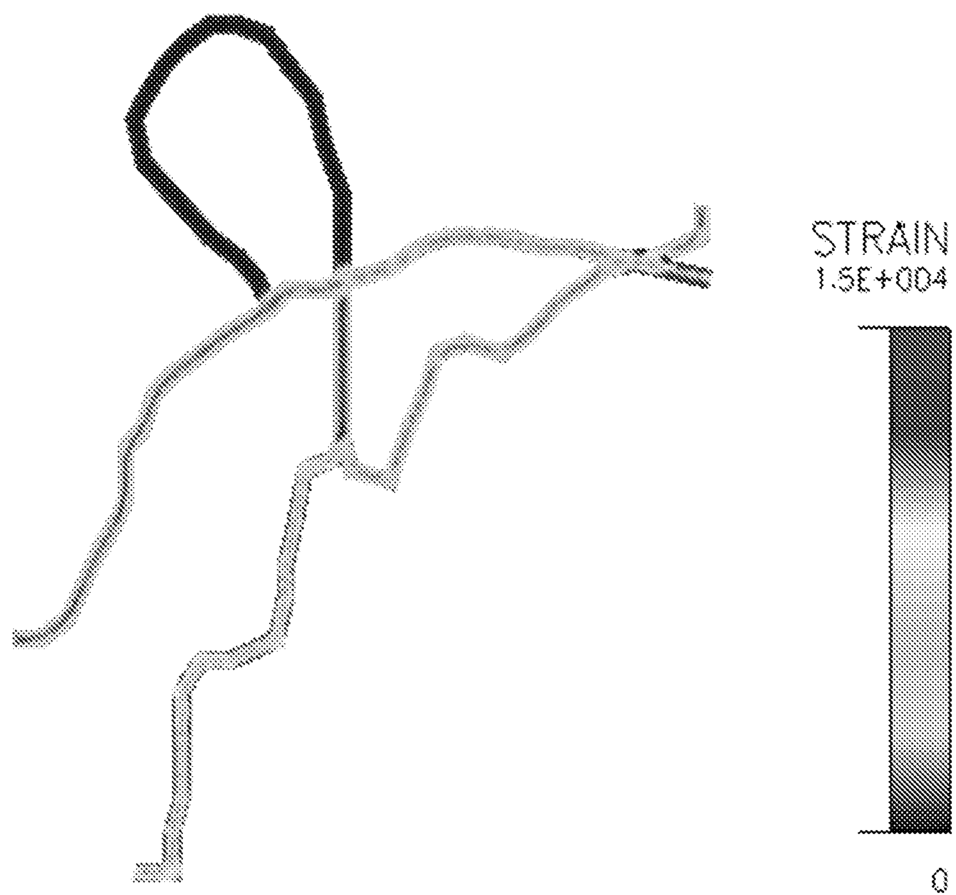

Digitized networks were imported directly into the commercial grid generation software tool CFD-GEOM®. CFD-GEOM®, which combines geometric modeling and various grid generation methodologies, was used to build the computational domains of these networks. The graphical user input software CFD-GUI® (ESI Group) was used to specify the simulation conditions. Following the completion of the simulations, the visualization software CFD-VIEW® (ESI Group) was used to visualize the obtained results. FIG. 5A shows the computational mesh corresponding to a microvascular network. FIGS. 5B and C show the results of computational analyses of the pressures and shear stresses within the microvascular network. The pressure and shear stress variations observed mimic those seen in-vivo and cannot be replicated using currently available flow chambers. The microcirculation networks used for these were about 30 μm in diameter. Flow rate was set such that the Reynolds number was 0.01.

Examples: Cell Culture in SMNs

Bovine Aortic Endothelial Cells (BAECs) were cultured in a SMN. BAECs were maintained in McCoy's 5A medium and allowed to grow to confluence in T25 flasks in an incubator at 37° C. and 5% $CO_2$. The cells were then trypisinized and resuspended in growth medium prior to use in the SMN. The SMN was perfused (15 μl/min) with physiological saline (30 min) followed by fibronectin (50 μg/ml, 90 min). The endothelial cells were then introduced into the system at a flow rate of 10 μl/min through the SMN for 1 min at a concentration of $1\times10^7$ cells/ml. The entire process was performed in a Type II/A2 laminar flow hood. During this procedure the fabricated networks were kept at 37° C. in a controlled, humidified chamber. The cells were then allowed to grow in an incubator at 37° C. and 5% $CO_2$. Cells were perfused daily with fresh media and were visualized for growth. Cells attached to the walls of the microvascular network at 8 hours post injection. By 12 hours, cells started to grow actively in the microvascular networks and were found to be confluent by 72 hours. The cells started to grow predominantly at junctions before spreading to other parts of the networks.

Figure 6:
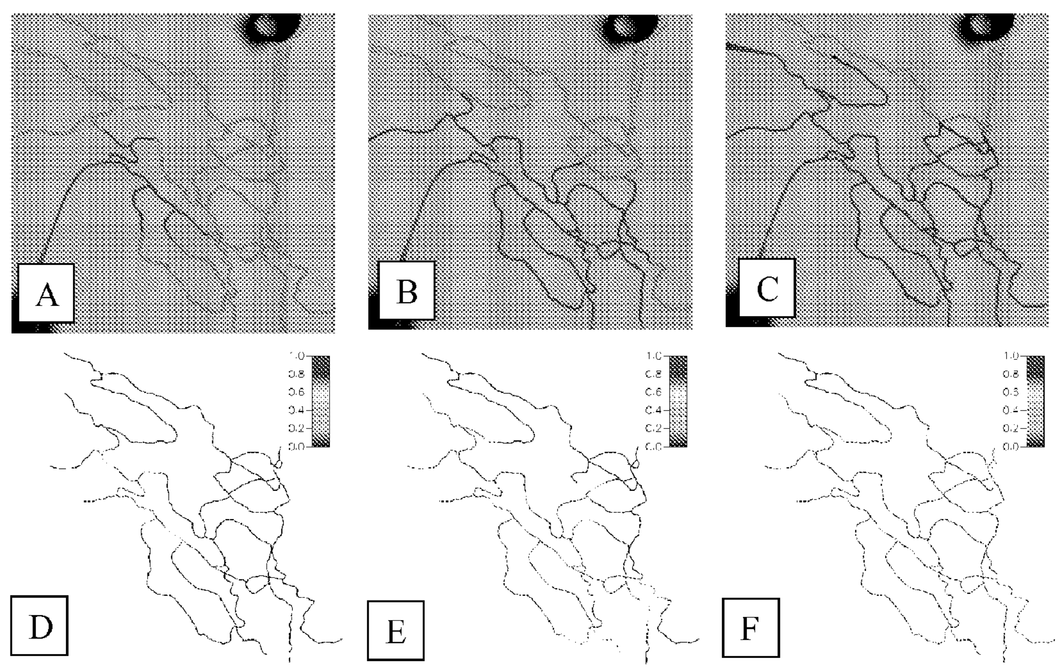
FIG. 6A-F Time serried comparison of actual and predicted flow through a SMN FIG. 7 Photo of a SMN identifying two junctions for flow analysis FIG. 8 Photo of flow analysis at first junction shown in FIG. 8

Examples: CFD Simulation of Perfusion in a Microvascular Network and Experimental Validation FIG. 6A-C is a time series of photos showing the perfusion map of a SMN following the introduction of the Trypan Blue. Simulation predictions of dye perfusion in the same network are also shown (FIG. 6D-F) for comparison. The network geometry in the simulation results was colored using an arbitrary concentration unit, which is shown in gray-scale in FIG. 6D-F. The path predicted by the simulations agrees very well with the actual path taken by Trypan Blue in the network. The results show that perfusion is spatially inhomogeneous and includes non-perfused stagnant regions that will affect particle transport and deposition/adhesion.

Figure 7:
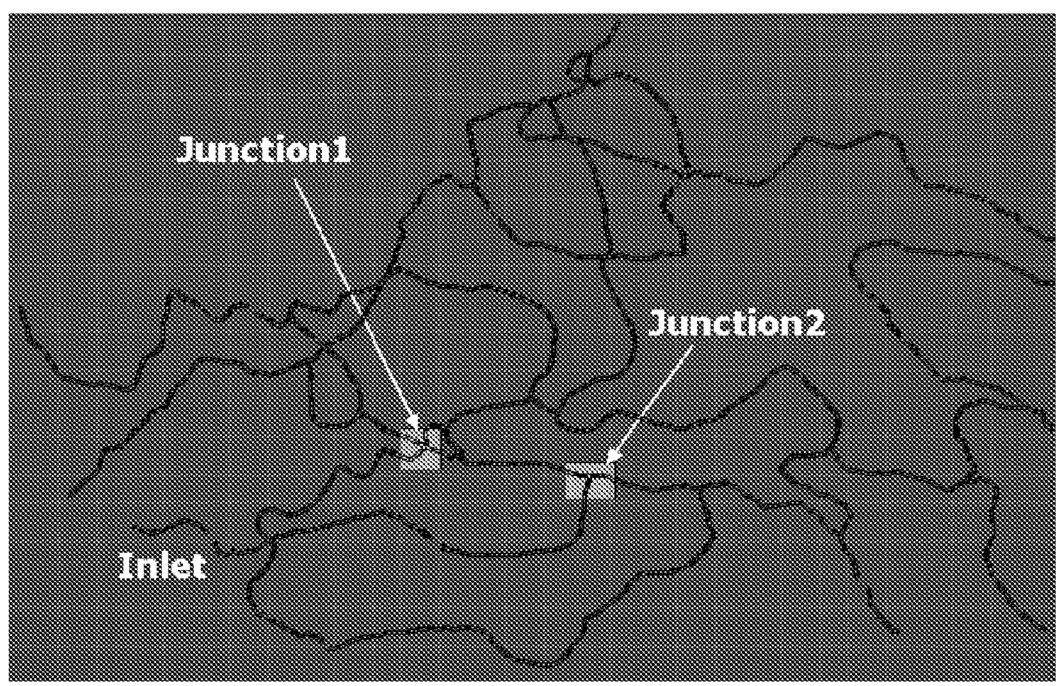
Figure 8:
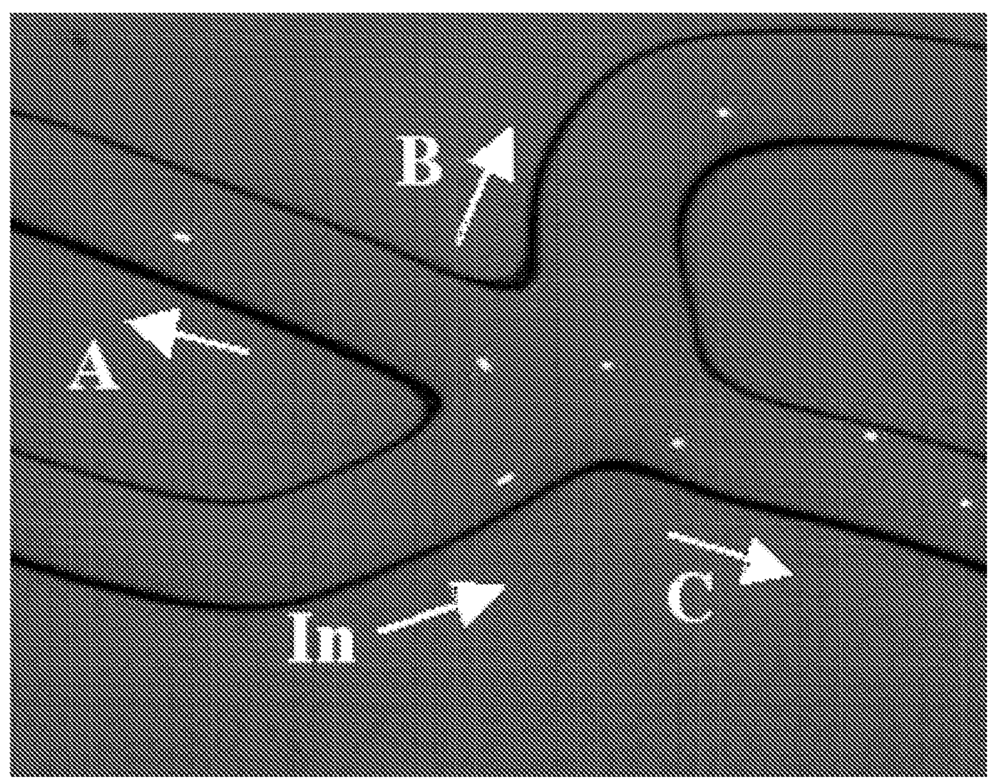
Figure 9:
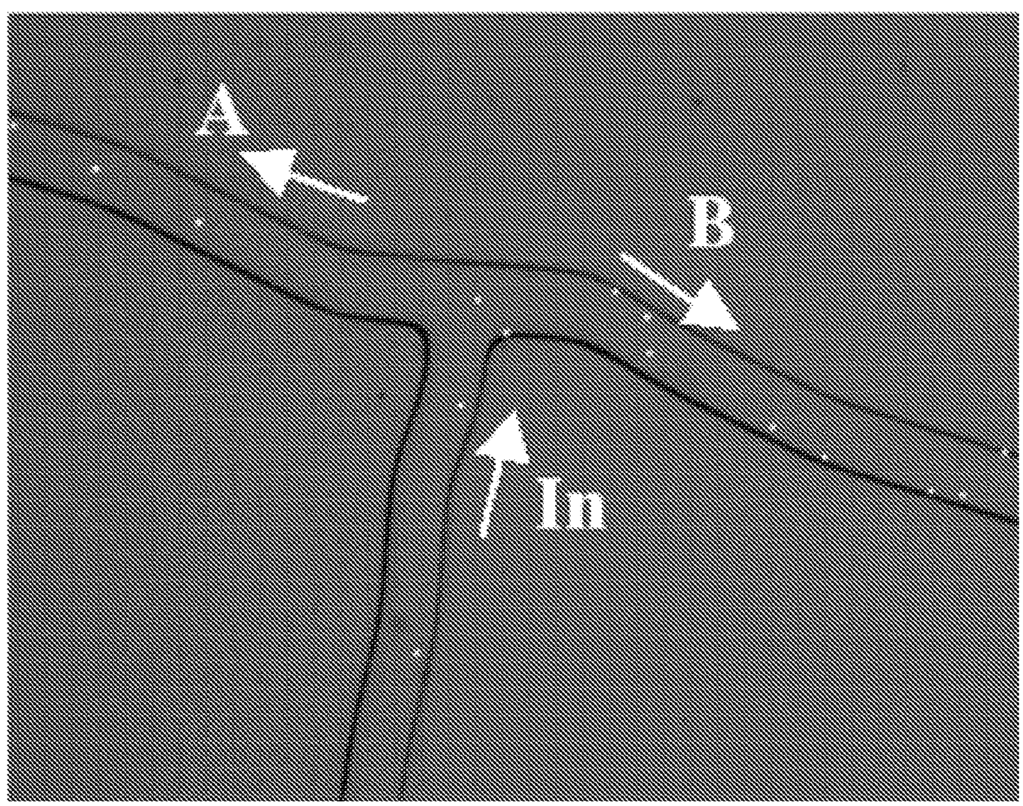
FIG. 9 Photo of flow analysis at second junction shown in FIG. 8
Figure 10:
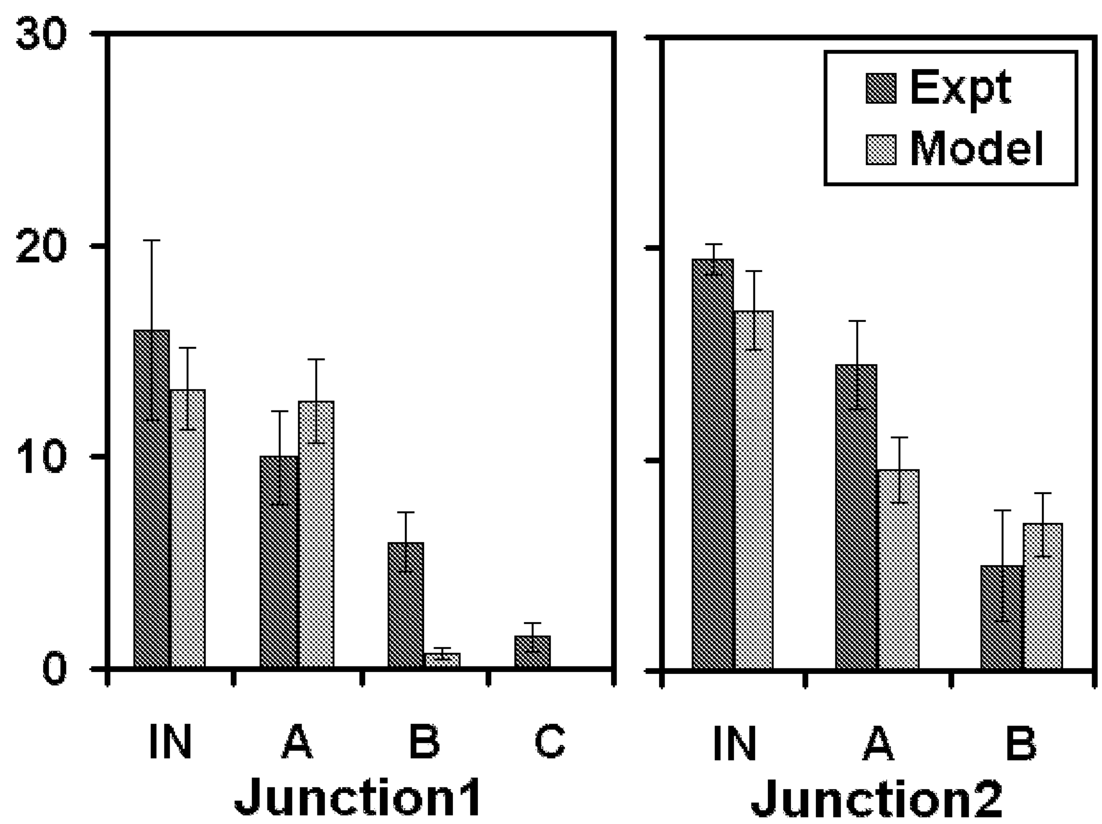
FIG. 10 Experimental and predicted particle fluxes at junctions 1 and 2
Figure 11:
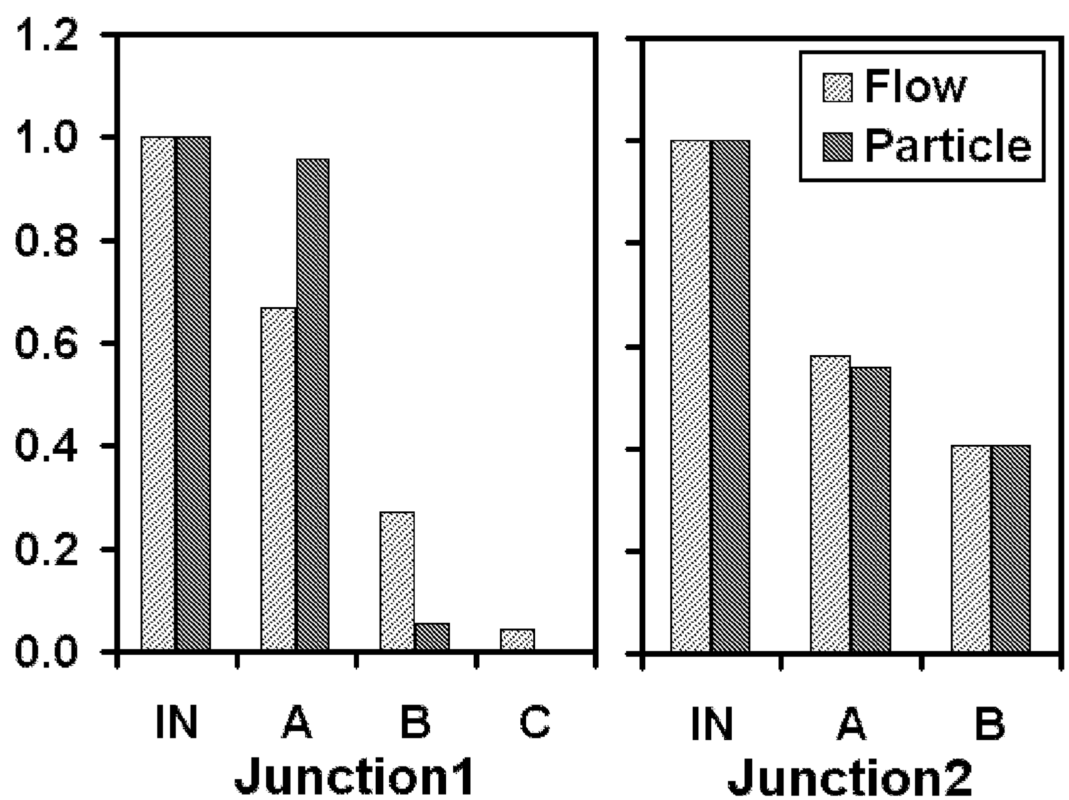
FIG. 11 Flow and particle split at junctions 1 and 2

Examples: CFD Simulation of Particle Transport and Adhesion in a SMN and Experimental Validation Particle transport at two junctions in the microvascular network shown in FIG. 7 is presented in FIG. 8 and FIG. 9. The direction of particle transport at the junction is indicated by arrows. Experimentally measured and numerically predicted values of particle flux at the two bifurcations shown in FIG. 8 and FIG. 9 are presented in FIG. 10. Fluid and particle flows are compared for both of the junctions in FIG. 11. The flow and particle ratios were defined with respect to the conditions in the arm labeled "In." While the particle split is nearly identical to the flow split at Junction 2, the flow/particle split is significantly different at Junction 1. These effects are representative of the complexities of the in-vivo environment and are clearly not realizable in existing parallel flow chambers.

Figure 12:
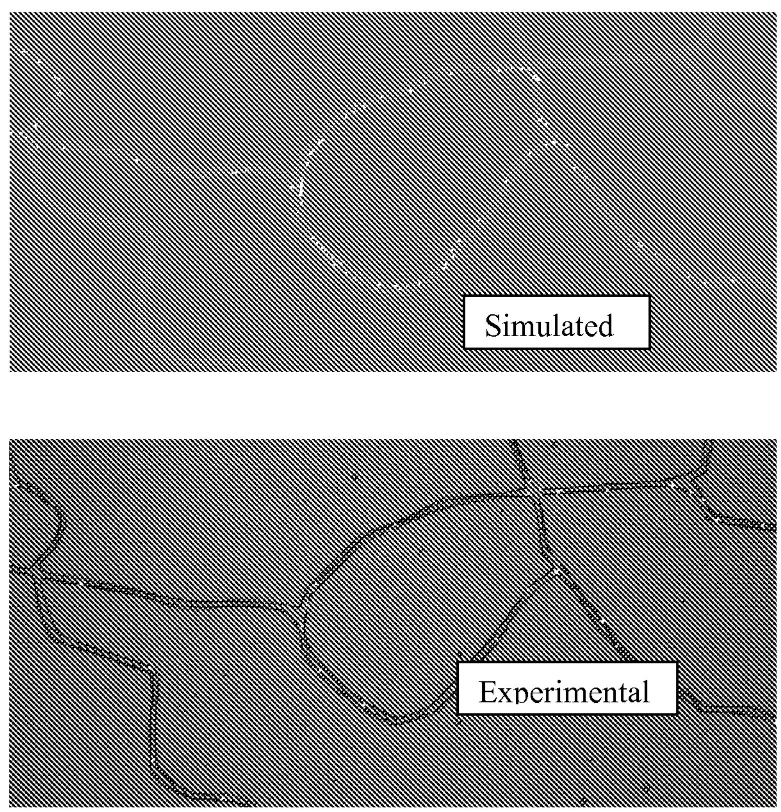
FIG. 12 Comparison of simulated and experimental particle adhesion in the same SMN

Particle adhesion in the SMN studies compared very well with simulated results. FIG. 12 compares particle adhesion occurring in a SMN with simulation results. Particle adhesion is enhanced in the bifurcations of the SMN in both cases and is in agreement with in-vivo experimental observations. Shear rate and flow rate maps generated by simulations of flow in the SMN were also generated. Particle adhesion patterns predicted by simulations correlated well with shear rate and velocity maps with low shear favoring adhesion and low particle flux inversely related to adhesion.

REFERENCES

Chang K C, Tees D F, Hammer D A, (2000) *The state diagram for cell adhesion under flow: leukocyte rolling and firm adhesion Proc Natl Acad Sci USA* 97(21):11262-7

Chapman G B, Cokelet G R (1998) *Flow resistance and drag forces due to multiple adherent leukocytes in postcapillary vessels Biophys J* 74(6):3292-301

Cokelet G R, Soave R, Pugh G, Rathbun L (1993) *Fabrication of in vitro microvascular blood flow systems by photolithography Microvasc Res* 46(3):394-400

Cozens-Roberts C, Quinn J A, Lauffenberger D A (1990) *Receptor-mediated adhesion phenomena. Model studies with the Radical-Flow Detachment Assay Biophys J* 58(1):107-25

Frame M D S, Sarelius I H (1995) *A system for culture of endothelial cells in* 20-50-μ*m branching tubes Microcirculation* 2(4):377-385

Goetz D J, el-Sabban M E, Pauli B U, Hammer D A (1994) *Dynamics of neutrophil rolling over stimulated endothelium in vitro Biophys J* 66(6):2202-9

Goldsmith H L, Turitto V T (1986) *Rheological aspects of thrombosis and haemostasis: basic principles and applications Thromb Haemost* 55(3):415-35

Hammer D A, Apte S M (1992) *Simulation of cell rolling and adhesion on surfaces in shear flow: general results and analysis of selectin-mediated neutrophil adhesion Biophys J* 63(1):35-57

House S D, Lipowsky H H (1988) *In vivo determination of the force of leukocyte-endothelium adhesion in the mesenteric microvasculature of the cat Circ. Res.* 63:658-668.

Kassab G S (2000) *The coronary vasculature and its reconstruction Ann Biomed Eng* 28(8):903

Lu H, Koo L Y, Wang W M, Lauffenburger D A, Griffith L G, Jensen K F (2004) *Microfluidic shear devices for quantitative analysis of cell adhesion Anal Chem* 76:5257-5264

Schmid-Schoenbein, G W, Fung, Y C, Zweifach B W (1975) *Vascular endothelium-leukocyte interaction; sticking shear force in venules Circ. Res.* 36:173-184

The invention claimed is:

1. A method for computationally simulating fluid flow through a microvascular network having one or more fluid inlets and one or more fluid outlets on a computer having a physical computer-readable medium having computer-executable instructions thereon that when executed by the computer implement the steps of the method, the method comprising:

a) creating a computational mesh representing the geometric features and connectivity of the microvascular network to generate a computational microvascular network, the computational microvascular network being selected from a physiological microvascular network, a synthetic microvascular network, and an averaged microvascular network;

b) specifying fluid flow/pressure conditions at the one or more inlets and one or more outlets; and c) solving for flow velocities and pressures using one or more mathematical models.

2. The method of claim 1, wherein the microvascular network is a physiological microvascular network.

3. The method of claim 1, wherein the microvascular network is a synthetic microvascular network having a network of nonlinear, interconnected flow channels in fluid communication with a network inlet and a network outlet, the network of non-linear, interconnected flow channels having a geometric characteristic selected from the group consisting of a variable cross-sectional shape, a variable cross-sectional area, a turn, a bend, a bifurcation, a junction, a convolution, an anastomosis, and combinations thereof.

4. The method of claim 1, wherein the microvascular network is an averaged microvascular network.

5. The method of claim 1, further comprising the steps of simulating particle adhesion in the microvascular network by:

d) specifying one or more physical and biological particle properties; and e) solving for particle transport using one or more mathematical models.

6. The method of claim 5, wherein the particle comprises a drug.

7. The method of claim 5, wherein data collected from particle adhesion experiments using synthetic microvascular networks is used to generate input for the one or more mathematical models.

8. The method of claim 7, wherein the data collected from particle adhesion experiments using synthetic microvascular networks is used for deconvolution of the flow dynamics and the adhesion process in the microvascular network.

9. The method of claim 1, comprising discretizing and solving the one or more mathematical models with a Finite Volume Method (FVM).

10. The method of claim 9, comprising computing a pressure-based integration of Navier-Stokes equations on arbitrary mesh topologies.

11. The method of claim 1, comprising calculating a converged solution for fluid flow by an iterative solution procedure.

12. The method of claim 1, the computational mesh being a three dimensional hybrid mesh including hexahedral and prismatic elements.

13. The method of claim 1, comprising:

obtaining a digitized microvascular network; and building computational domains of the digitized microvascular network.

14. The method of claim 13, wherein the digitized microvascular network including data for one or more of: inlet branches, outlet branches, flow rates, shear stress, diameter, distance between nodes, and vessel length.

15. The method of claim 1, comprising calculating pressures and shear stresses within the computational microvascular network.

16. The method of claim 1, comprising generating shear rate and flow rate maps of the computational microvascular network.

17. The method of claim 5, comprising extracting predictive relationships between two or more of flow rate, particle size, receptor density, and network geometry.

18. The method of claim 5, the one or more mathematical models used for solving for particle transport including one or more of:

shear-induced lift forces;

particle-wall lubrication effects;

nanoparticle and/or porous particle transport;

particle-particle interactions; and abstraction of reduced order adhesion models.

19. The method of claim 5, comprising computing particle collisions based on physical proximity of neighboring particles.

20. The method of claim 5, comprising comparing fluid and particle flows at one or more junctions of the computational microvascular network.

* * * * *